(12) United States Patent
Fisk

(10) Patent No.: US 9,297,787 B2
(45) Date of Patent: Mar. 29, 2016

(54) AUTOMATIC SONIC/ULTRASONIC DATA ACQUISITION SYSTEM FOR EVALUATING THE CONDITION AND INTEGRITY OF CONCRETE STRUCTURES SUCH AS RAILROAD TIES

(71) Applicant: Paul Fisk, Princeton, MA (US)

(72) Inventor: Paul Fisk, Princeton, MA (US)

( * ) Notice: Subject to any disclaimer, the term of this patent is extended or adjusted under 35 U.S.C. 154(b) by 346 days.

(21) Appl. No.: 13/971,086

(22) Filed: Aug. 20, 2013

(65) Prior Publication Data

US 2014/0345387 A1     Nov. 27, 2014

Related U.S. Application Data

(63) Continuation-in-part of application No. 13/901,600, filed on May 24, 2013, now abandoned.

(60) Provisional application No. 61/651,629, filed on May 25, 2012.

(51) Int. Cl.
  *G01N 29/04* (2006.01)
  *G01N 29/265* (2006.01)

(52) U.S. Cl.
  CPC ............ *G01N 29/041* (2013.01); *G01N 29/265* (2013.01); *G01N 2291/2623* (2013.01)

(58) Field of Classification Search
  USPC .................................................. 73/636, 635
  See application file for complete search history.

(56) References Cited

U.S. PATENT DOCUMENTS

| | | | | |
|---|---|---|---|---|
| 4,044,594 A | * | 8/1977 | Owens | B61K 9/10 73/621 |
| 4,932,618 A | * | 6/1990 | Davenport | B61L 23/042 180/169 |
| 5,275,051 A | * | 1/1994 | De Beer | G01N 29/07 73/598 |
| 6,981,419 B1 | * | 1/2006 | Hay | G01N 29/226 73/636 |
| 2011/0154902 A1 | * | 6/2011 | Fisk | G01N 29/265 73/592 |
| 2013/0276539 A1 | * | 10/2013 | Wagner | G01N 33/383 73/595 |

* cited by examiner

*Primary Examiner* — Hezron E Williams
*Assistant Examiner* — Xin Zhong
(74) *Attorney, Agent, or Firm* — Brian M. Dingman; Dingman, McInnes & McLane, LLP

(57) ABSTRACT

An automatic sonic/ultrasonic data acquisition system for collecting data from concrete railroad ties. The system has a frame, a wheel carried by the frame and constructed and arranged to rotate relative to the frame such that the wheel can roll along the top of a rail, an axle suspended from the frame and adapted to be rotated relative to the frame via rotation of the wheel, one or more sensors coupled to the axle and constructed and arranged to contact the ties as the frame is moved along the rails, and an energy source for initiating in the ties compressional and/or shear/Rayleigh waves that are sensed by the sensors.

12 Claims, 4 Drawing Sheets

AUTOMATIC SONIC/ULTRASONIC DATA ACQUISITION SYSTEM FOR EVALUATING THE CONDITION AND INTEGRITY OF CONCRETE STRUCTURES SUCH AS RAILROAD TIES

CROSS-REFERENCE TO RELATED APPLICATIONS

This application claims priority of Non-Provisional patent application Ser. No. 13/901,600 filed on May 24, 2013, which itself claims priority of Provisional Patent Application No. 61/651,629 filed on May 25, 2012.

BACKGROUND

Measurements of the velocity that compressional and shear/Rayleigh waves propagate along and through concrete and impact echo thickness resonant frequencies have been used to evaluate the integrity and condition of concrete structures. For this technology to be cost effective in the evaluation of concrete railroad cross ties, test data has to be acquired rapidly and systematically.

SUMMARY

Figure 1:
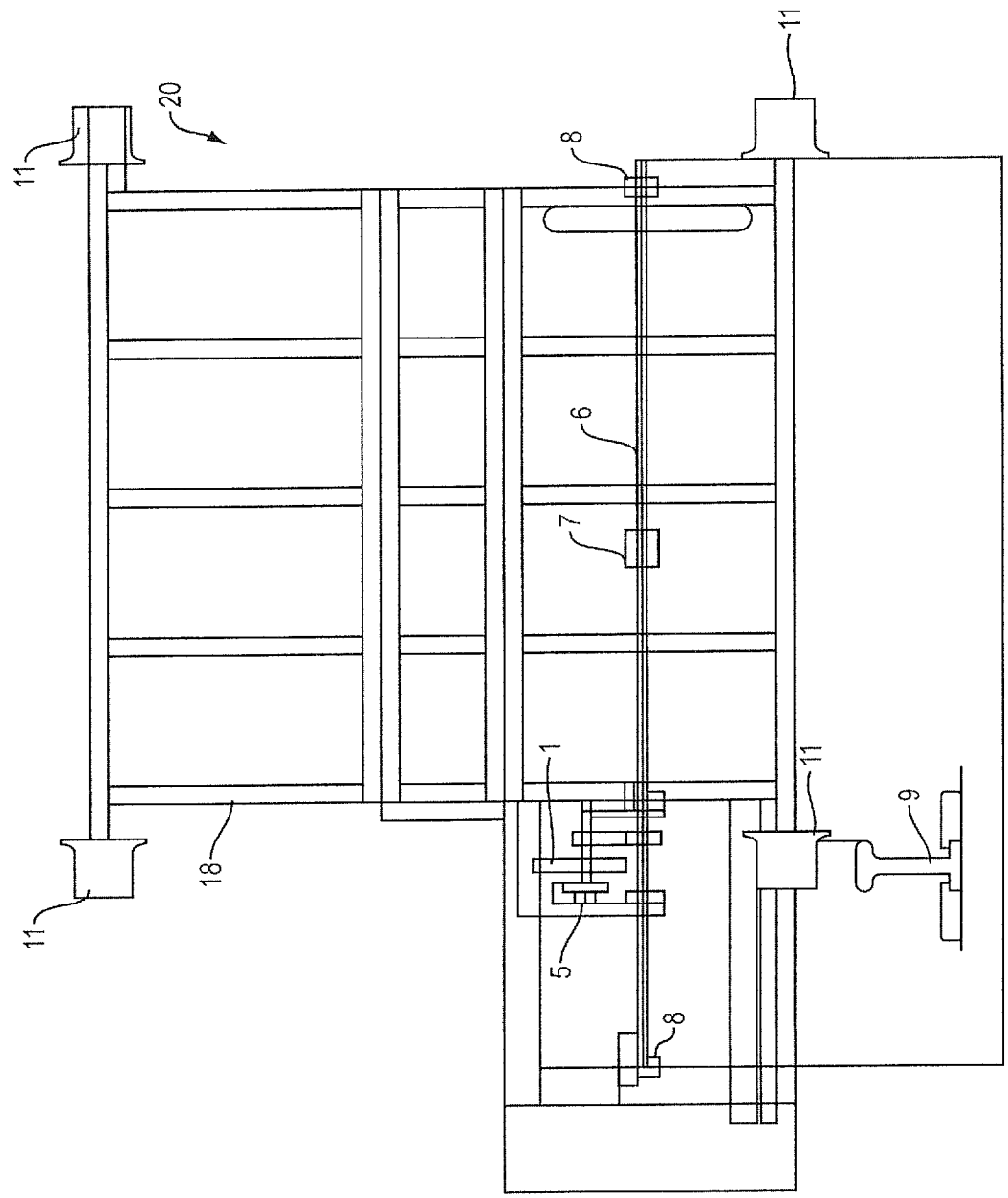
FIG. 1 is a top schematic view of an automatic sonic/ultrasonic data acquisition system for evaluating the condition and integrity of concrete railroad ties.

This disclosure includes a device or system that is constructed and arranged to be moved along a rail line and automatically acquire sonic/ultrasonic time series data on the concrete railroad ties. The device may also be useful for collecting such data on other types of concrete structures.

This disclosure features an automatic sonic/ultrasonic data acquisition system for collecting data from concrete railroad ties that support rails, comprising a frame, a wheel carried by the frame and constructed and arranged to rotate relative to the frame such that the wheel can roll along the top of a rail, an axle suspended from the frame and adapted to be rotated relative to the frame via rotation of the wheel, one or more sensors coupled to the axle and constructed and arranged to contact the ties as the frame is moved along the rails, and an energy source for initiating in the ties compressional and/or shear/Rayleigh waves that are sensed by the sensors. There may be at least two sensors for each tie. A tie may support two spaced rails and there may be at least four sensors, where the sensors are arranged such that a sensor contacts the tie close to each side of each rail. The axle may be rotated by a drive belt that is driven by the wheel rotation. The drive belt may be engaged with a sprocket carried by the wheel. The sprocket may be generally elliptical and have two opposed flatter sides and two opposed narrower ends. The sensors may be coupled to the axle in such a manner that a sensor is on a tie when the drive belt is engaged with a flatter side of the sprocket.

DESCRIPTION OF EXAMPLES

This disclosure includes a device or system that is constructed and arranged to be moved along a rail line and automatically acquire sonic/ultrasonic time series data on the concrete railroad ties. System 20 is comprised of a drive wheel 1 that rides on top of a rail 9 (using wheels 11) and drives an axle 6 that is suspended from a vehicle 18 that rolls on the rails; one example of an appropriate vehicle 18 is a TS Series Cart from The Nolan Company of Canton, Ohio, which is a lightweight rail vehicle. Drive wheel 1 is coupled to the cart and also rolls on a rail; wheel 1 rotates axle 6 (e.g., using drive belt 15) in such a manner that there is one full rotation every two feet, which is the distance between concrete cross ties. Passive pressure transducers 2 (e.g., piezoelectric-based devices) are mounted at the ends of adjustable length sensor holders 3 that are attached to the axle. The axle rotation caused by movement of the cart along the rails thus automatically positions the sensors at the top of each tie 13.

A projectile impact energy source 4 causes a projectile such as a ball bearing to impact the tie, which generates a sonic/ultrasonic signal. Energy source 4 activated by a laser photo interrupt 5. Interrupt 5 is timed so that it activates when the sensors roll into position on the surface of the tie. The pressure transducers are mounted in the sensor holders 3 with a rubber backing that acoustically isolates the sensor from the rest of the system and applies approximately 5 to 10 pounds of back pressure to push the sensor against the tie. Sonic/ultrasonic signals recorded by the sensors are communicated by wire through the axle from the sensors through a slip ring assembly 7, to an A/D converter and a signal processing card and/or other electronic device(s) (not shown) that process and potentially store and/or further communicate the sensor signals, e.g., to a storage or signal processing system. End bearings 8 support the axle so that it rotates easily and smoothly. Bearings 8 also serve as mounting points for the axle to the frame of the Nolan Cart.

Figure 2:
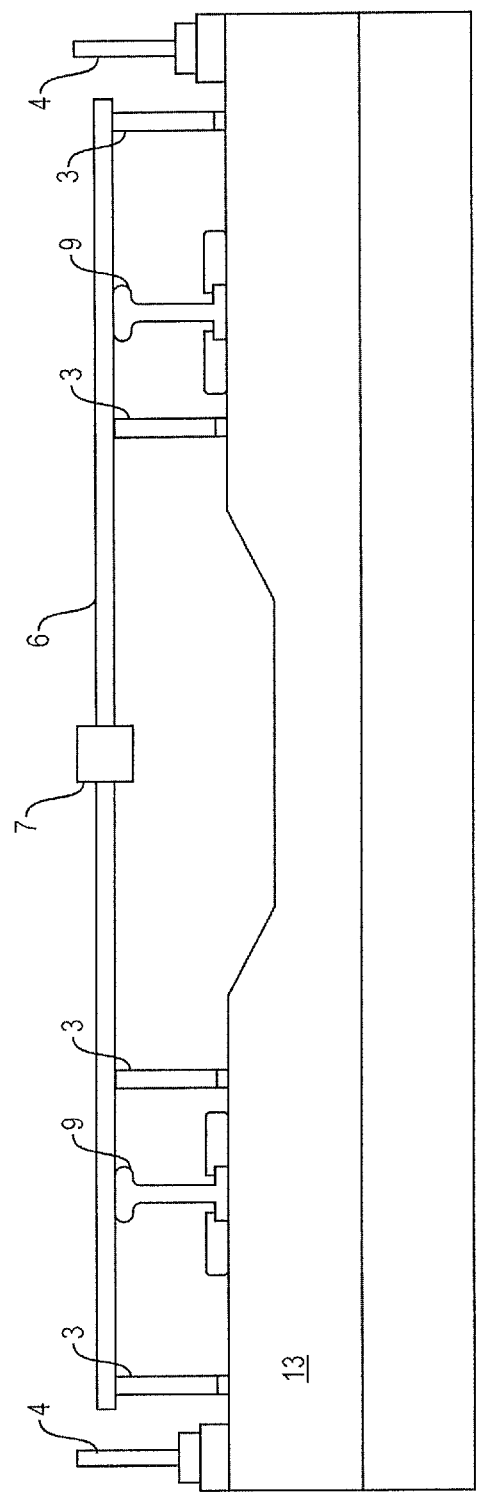
FIG. 2 is a side view of part of the system of FIG. 1.
Figure 3:
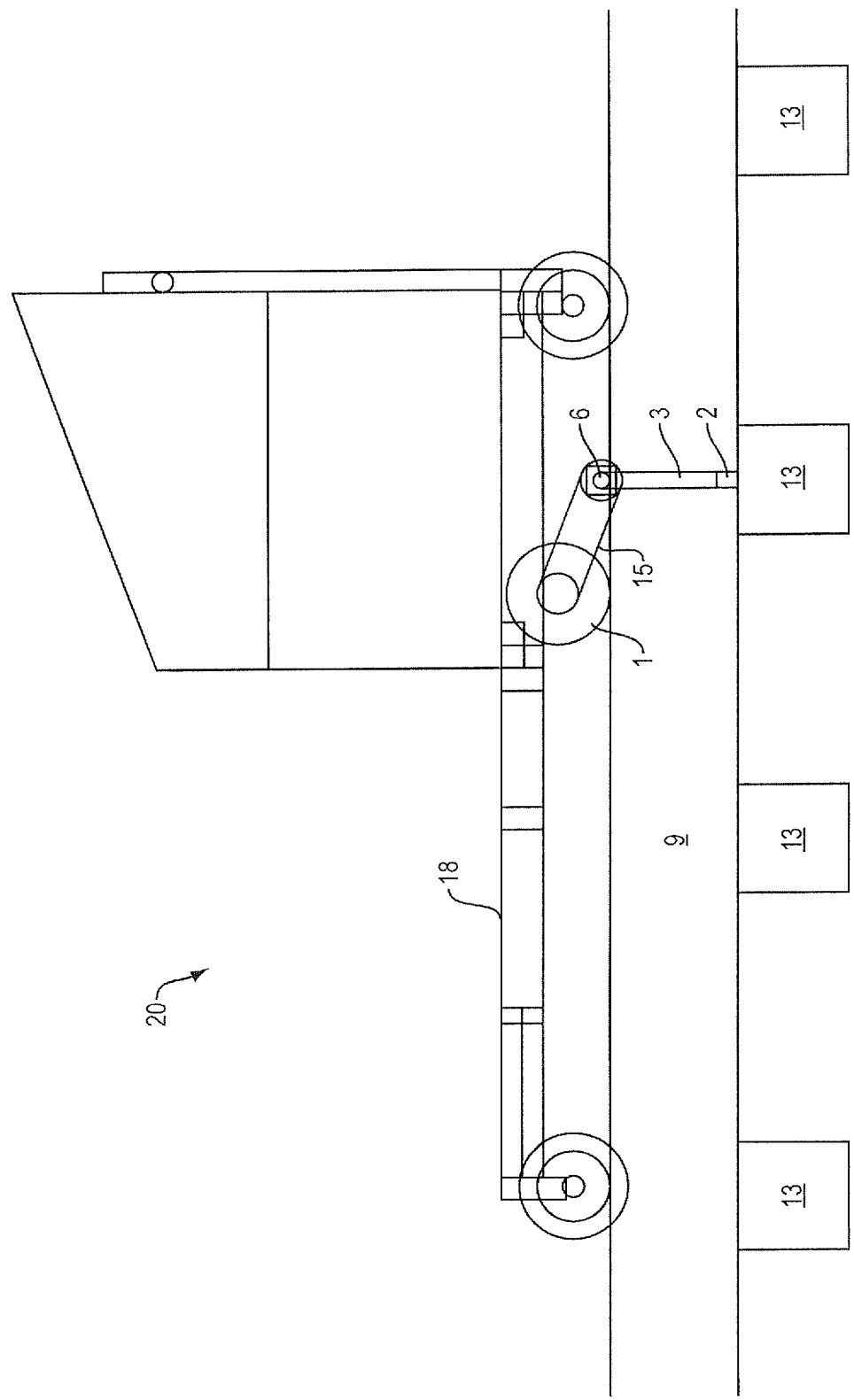
FIG. 3 is a side view of the system of FIG. 1.

In one non-limiting embodiment there are at least four sensors (one close to each side of each of the two rails so that the areas underneath and proximate the rails that see the most stress are tested) and two impact energy sources 4, one at each end of the tie, as shown in FIG. 2.

Operation

The Nolan cart is moved along the rails. The drive wheel riding on top of a rail rotates a drive belt attached to the axle so that the axle has one full rotation every two feet. One or more pressure transducers mounted in sensor holders attached to the axle rotate so that the sensors come in contact with the top of the concrete tie. There is preferably one sensor close to either side of each rail. Alternatively, there may be one sensor per tie, or more than two sensors per tie. A slotted photo interrupt mounted on the axle of the drive wheel allows a laser signal to pass at a predetermined timing. The laser signal is received by a receiver which is then used to signal the sonic/ultrasonic energy source(s) to initiate. The energy source may be a compressed gas-operated pistol that fires a ball bearing that impacts the tie. Signals recorded by the pressure transducer sensors are communicated by wires through the sensor mounts and axle to a slip ring in the middle of the axle.

Second Example

Figure 4:
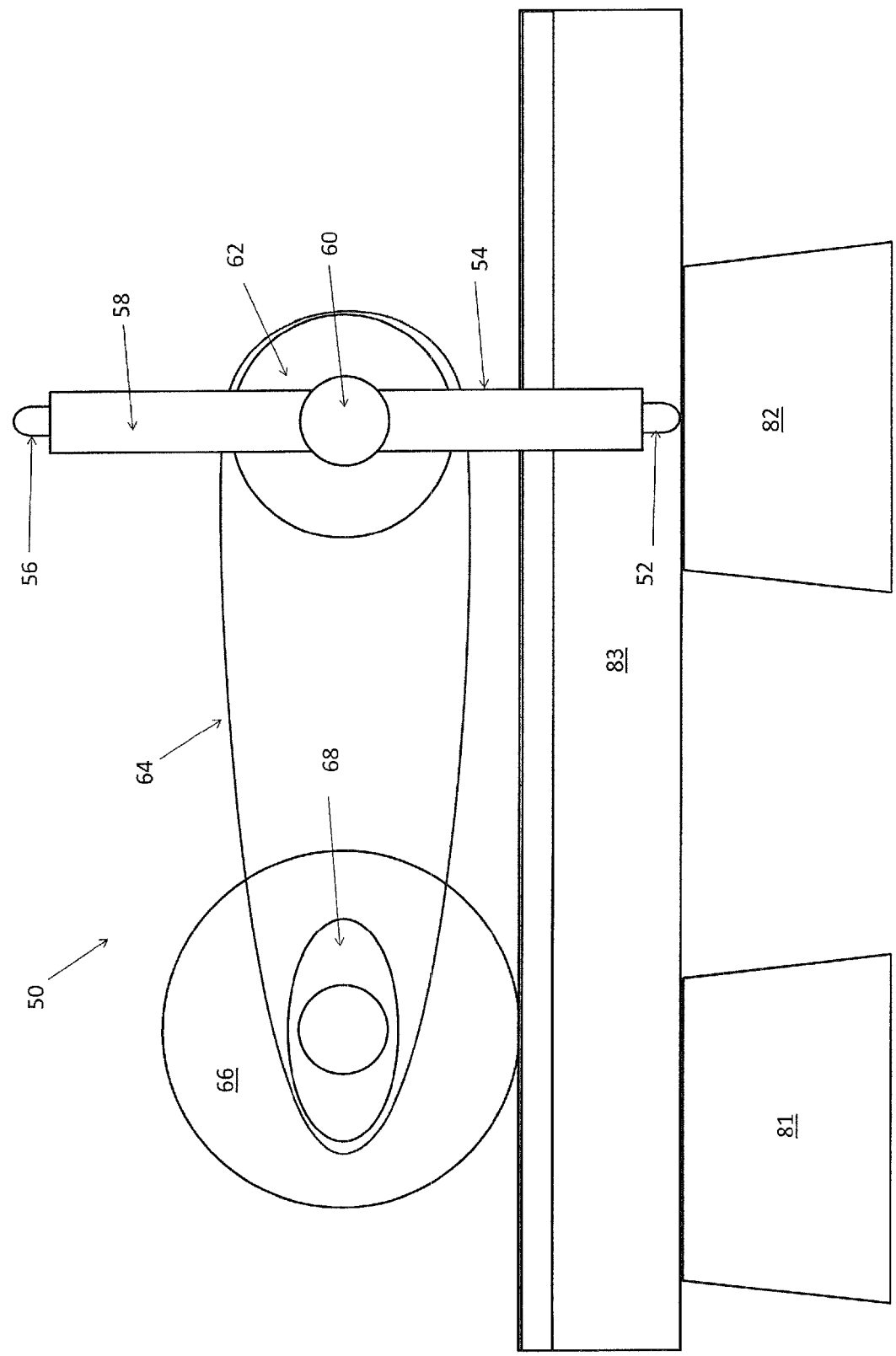
FIG. 4 is a partial side schematic view of another automatic sonic/ultrasonic data acquisition system for evaluating the condition and integrity of concrete railroad ties.

A second example is shown in FIG. 4. System 50 is similar to system 20. Sensors 52 and 56 at the ends of sensor holders 54 and 58 are adapted to contact the top of ties 81 and 82 that support rail 83. Axle 60 supports holders 54 and 58. Axle 60 is coupled to driven sprocket 62 which is rotated by grooved drive belt 64 that engages with drive sprocket 68 that is carried by drive wheel 66; drive wheel 66 rolls along rail 83. The difference here as compared to system 20 is primarily that sprocket 68 is elliptical rather than round. The elliptical sprocket creates an different rotation rate of sprocket 62 depending on the position of the elliptical sprocket. The sensors are positioned such that the drive belt is engaged with a flat side of sprocket 68 when the sensor is in contact with a tie. A result is that the sensors will dwell longer on the top of the tie as compared to with system 20 that uses a round drive sprocket.

Although aspects of the invention are shown in some drawings and not others, this is not a limitation as the features can be combined in any technically feasible way. And other embodiments will occur to those skilled in the technical field. For example, the device/system can be used to test concrete structures other than railroad ties.

What is claimed is:

1. An automatic sonic/ultrasonic data acquisition system for collecting data from concrete railroad ties that support rails, comprising;
   a frame;
   a wheel carried by the frame and constructed and arranged to rotate relative to the frame such that the wheel can roll along the top of a rail;
   an axle suspended from the frame and adapted to be rotated relative to the frame via rotation of the wheel;
   one or more sensors coupled to the axle and constructed and arranged to contact the ties as the frame is moved along the rails; and
   an energy source for initiating in the ties compressional and/or shear/Rayleigh waves that are sensed by the sensors;
   wherein the axle is rotated by a drive belt that is driven by the wheel rotation and the drive belt is engaged with a sprocket carried by the wheel; and,
   wherein the sprocket is generally elliptical and has two opposed flatter sides and two opposed narrower ends.

2. The system of claim 1 in which the sensors are coupled to the axle in such a manner that a sensor is on a tie when the drive belt is engaged with a flatter side of the sprocket.

3. The system of claim 1 wherein the one or more the sensors are mounted on adjustable length sensor holders.

4. The system of claim 1 wherein the one or more the sensors are mounted to one or more corresponding sensor holders with a backing that acoustically isolates the sensors from the rest of the system.

5. The system of claim 1 wherein the one or more the sensors are held against the tie from which data is to be collected with 5-10 lbs. of back pressure.

6. The system of claim 1 wherein the one or more sensors are piezoelectric sensors.

7. The system of claim 1 in which there are at least two sensors for each tie.

8. The system of claim 7 wherein a tie supports first and second spaced rails and there are at least four sensors, where the sensors are arranged such that first and second sensors contacts the tie close to each side of the first rail, and third and fourth sensors contact the tie close to each side of the second rail.

9. The system of claim 1 wherein the energy source is a projectile impact energy source.

10. The system of claim 9 further comprising a second projectile impact energy source, wherein the first projectile impact energy source is constructed and arranged to be located at a first end of a tie from which data is to be collected and the second projectile impact energy source is located at a second end of the tie from which data is to be collected.

11. The system of claim 1 wherein the one or more sensors are pressure sensors.

12. The system of claim 11 wherein the one or more sensors are piezoelectric sensors.

* * * * *